United States Patent
Lawandy

(10) Patent No.: US 6,233,481 B1
(45) Date of Patent: May 15, 2001

(54) DIAGNOSTIC APPLICATION OF SONO-CHEMICAL EXCITATION OF FLUORESCENT PHOTOSENSITIZERS

(75) Inventor: Nabil M Lawandy, North Kingstown, RI (US)

(73) Assignee: Spectra Science Corporation, Providence, RI (US)

(*) Notice: Subject to any disclaimer, the term of this patent is extended or adjusted under 35 U.S.C. 154(b) by 0 days.

(21) Appl. No.: 09/166,408

(22) Filed: Oct. 5, 1998

Related U.S. Application Data

(60) Provisional application No. 60/061,490, filed on Oct. 9, 1997.

(51) Int. Cl.[7] ............................................. A61B 6/00
(52) U.S. Cl. ............................. 600/476; 604/20; 604/22; 600/437
(58) Field of Search ................................... 600/476, 407, 600/437, 473, 474, 1, 2; 604/20, 22; 128/21, 890.1, 890.2

(56) References Cited

U.S. PATENT DOCUMENTS

| | | | |
|---|---|---|---|
| 4,889,129 | 12/1989 | Dougherty | 128/664 |
| 4,917,084 | 4/1990 | Sinofsky | 606/7 |
| 4,930,504 | 6/1990 | Diamantopoulos et al. | 128/395 |
| 4,957,481 | 9/1990 | Gatenby | 604/20 |
| 5,092,841 | 3/1992 | Spears | 604/96 |
| 5,111,821 | 5/1992 | Potter | 128/654 |
| 5,498,710 * | 3/1996 | Pandey et al. | 540/145 |
| 5,527,350 | 6/1996 | Grove et al. | 607/89 |
| 5,572,996 | 11/1996 | Doiron et al. | 128/633 |
| 5,625,456 | 4/1997 | Lawandy | 356/376 |
| 5,817,048 * | 10/1998 | Lawandy | 604/20 |

\* cited by examiner

Primary Examiner—Marvin M. Lateef
Assistant Examiner—Jeoyuh Lin
(74) Attorney, Agent, or Firm—Ohlandt, Greeley, Ruggiero & Perle, LLP

(57) ABSTRACT

Disclosed is a method for generating an image of a selected area of tissue, the method includes steps of: (a) providing a fluorescent photosensitizer compound in combination with a hydrogen-containing solvent to the selected area of tissue; (b) generating acoustic energy for generating free radicals from the solvent; (c) reacting the free radicals with an oxalate ester to generate a key intermediate; (d) transferring chemical energy to the fluorescent photosensitizer compound from the key intermediate; (e) activating the fluorescent photosensitizer compound with the transferred energy to emit long wavelength light; and (f) detecting the long wavelength light to generate the image of the selected area of tissue. In one embodiment the oxalate ester is comprised of ester bis (2,4-dinitrophenyl) oxalate (DNPO). In one application, a selected area of living tissue is analyzed to identify an abnormality within the tissue.

16 Claims, 3 Drawing Sheets

○ OXALATE ESTERS OR OXAMIDES
⊘ PHOTOSENSITIZERS/FLUORESCERS

○ OXALATE ESTERS
⊘ PHOTOSENSITIZERS

DIAGNOSTIC APPLICATION OF SONO-CHEMICAL EXCITATION OF FLUORESCENT PHOTOSENSITIZERS

CROSS-REFERENCE TO RELATED APPLICATIONS

Priority is herewith claimed under 35 U.S.C. §119(e) from copending Provisional Patent Application No. 60/061,490, filed Oct. 9, 1997, entitled "Diagnostic Application of Sonochemical Excitation of Fluorescent Photosensetizer", by Nabil M. Lawandy. The disclosure of this Provisional Patent Application is incorporated by reference herein in its entirety. This patent application is related to commonly assigned U.S. patent application Ser. No. 08/821,088, filed Mar. 20, 1997, entitled "Ultrasonic Alternative to Laser-Based Photodynamic Therapy", by Nabil M. Lawandy, now U.S. Pat. No. 5,817,048, issued Oct. 6, 1998. This patent application is also related to commonly assigned U.S. patent application Ser. No. 08/929,782, filed Sep. 15, 1997, entitled "Chemiluminescent Sources For Photodynamic Therapy and Photomedicine", by Nabil M. Lawandy. The disclosure of this U.S. Patent and this U.S. Patent Application are incorporated by reference herein in their entireties.

FIELD OF THE INVENTION

This invention relates generally to diagnostic procedures used in the treatment of abnormal cell tissue.

BACKGROUND OF THE INVENTION

As is made evident in the above-referenced U.S. Patent, in the treatment of cancer and macular degeneration with photodynamic therapy (PDT), a class of photosensitizing compounds has been developed by a number of drug companies that are either selectively retained in, or are preferentially produced by, rapidly dividing cells. These dye-like molecules, when exposed to laser light in the visible or UV region, are excited to the triplet state where they have the capacity to promote molecular oxygen to its first excited singlet ($^1O_2$). This species of molecular oxygen is believed to be cytotoxic and to cause local necrosis of tumor cells.

One particular drawback of the technique, however, is the limit in penetration depth inherent in using visible light as an activation mechanism. Additionally, the use of lasers or lamps as an activation source may require the use of expensive or complicated delivery systems. Furthermore, diagnosis and treatment of internal cancer sites may be invasive, and require the use of fiber optic catheters, endoscopes, or similar instruments.

Similar problems can arise when performing a diagnostic procedure to determine a presence of and/or location of abnormal cell tissue.

OBJECTS OF THE INVENTION

It is a first object and advantage of this invention to provide an improved method for performing a diagnostic technique that overcomes the foregoing and other problems.

It is another object and advantage of this invention to provide an improved method for activating fluorescent photosensitizer compounds, the improved method employing ultrasonic energy.

It is a further object and advantage of this invention to provide an improved method for activating fluorescent photosensitizer compounds, the improved method employing focused and scanned ultrasonic energy that triggers chemiluminescent reactions which emit detectable long wavelength light.

Further objects and advantages of this invention will become more apparent from a consideration of the drawings and ensuing description.

SUMMARY OF THE INVENTION

The foregoing and other problems are overcome and the objects and advantages are realized by methods and apparatus in accordance with embodiments of this invention.

In accordance with the present invention a method for generating an image of a selected area of tissue includes the steps of: (a) providing a fluorescent photosensitizer compound in combination with a hydrogen-containing solvent to the selected area of tissue; (b) generating acoustic energy for generating free radicals from the solvent; (c) reacting the free radicals with an oxalate ester to generate a key intermediate; (d) transferring chemical energy to the fluorescent photosensitizer compound from the key intermediate; (e) activating the fluorescent photosensitizer compound with the transferred energy to emit long wavelength light; and (f) detecting the long wavelength light to generate the image of the selected area of tissue. The long wavelength light is radiation in a range of wavelengths that is greater than ultraviolet radiation wavelengths.

In one embodiment, the selected area of tissue is a selected area of living tissue, and the method includes a further step of analyzing the image to identify a tumor within the living tissue.

An imaging apparatus is also disclosed wherein a selected area of tissue may be analyzed for the presence of a tumor.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 1:
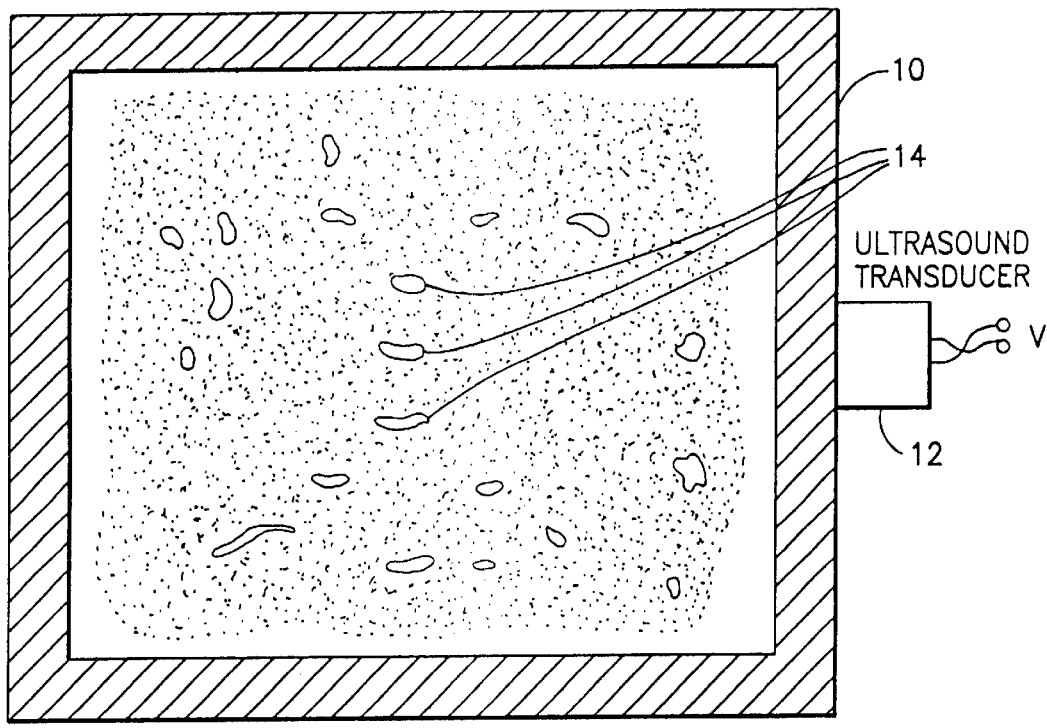
FIG. 1 depicts an ultrasound chamber and shows chemiluminescent emission from anti-nodes of an ultrasound field within the chamber.

In the present invention sono-chemical excitation of fluorescent photosensitizers is employed in the diagnosis and treatment of cancer. In particular, the inventor has realized that the application of focused and scanned acoustic energy, in particular ultrasound energy, activates fluorescent photosensitizer compounds to trigger chemiluminescent reactions which emit long wavelength light. The long wavelength light is defined as radiation in a range of wavelengths that is greater than ultraviolet radiation wavelengths, i.e. greater than about 390 nm. Preferably, the emission wavelengths minimize the absorption of the emission by blood and melanin, i.e. the absorption of the emission by the tissue under diagnosis or treatment and/or intervening tissue between the area of interest and the skin's surface.

In diagnostic applications, the emissions are detected to permit the identification of cancer cells or cancer tumors within a subject tissue. The detected emissions may also be imaged to permit a visual inspection of the subject tissue. In treatment applications, as disclosed in the above-identified U.S. patent and copending U.S. patent application, the emissions transfer energy to specifically designed PDT drugs which selectively destroy cells within an area of tissue to be treated.

The present invention has been shown to produce satisfactory results by applying ultrasonic energy to, for example, peroxyoxalate chemiluminescent systems (PO CL). In these chemiluminescent systems, oxalic acid derivatives react with, for example, hydrogen peroxide ($H_2O_2$) in the presence of a fluorophore to produce a bright emission characteristic of the fluorescer. This reaction proceeds via an energetic key intermediate, for example, 1,2-dioxetanedione.

Suitable oxalate esters for use in the present invention include the following:
Bis(2-nitrophenyl)
Bis(4-nitrophenyl)
Bis(4-nitro 3-trifluoromethyl)
Bis(4-nitro-2-formylphenyl)
Bis(4-nitro-2,6-dichlorophenyl)
Bis(2,4-dinitrophenyl)
Bis(2,5-dinitrophenyl)
Bis(2,4-dichlorophenyl)
Bis(pentacholorophenyl)
Bis(pentafluorophenyl)
Bis(3-trifluoro-methylphenyl)
Bis(3,5-di(trifluoro-methylphenyl)
Bis(2,6-dimethylphenyl)
Bis(4-methoxyphenyl)
Diphenyl
Phenylene
Bis(2-naphthyl)
Di-i-butyl
Bis(2-cyano-2-propyl)
Bis(2,2,2-trifluoro-ethyl
Bis(diphenylmethyl)

Another oxalate ester of interest is bis(2,4,6-trichlorophenyl) oxalate.

Suitable fluorescers for use with this invention include the following:
Coumarin 440
Coumarin 480
9,10-diphenylanthracene (DPA)
Rhodamine 590
Rhodamine 610
Rhodamine 640
Rhodamine tetrafluoroborate
Sulforhodamine 640
DCM
Kiton red 620
Acridine orange The enhancement capacity of $TiO_2$ for different dyes (Ester, dye+Peroxide with and without $TiO_2$) was confirmed for the following:
Rubrene (yellow emission)
9,10-bis(phenylethynyl)anthracene (yellow)
Coumarin 480 (blue)
9,10-diphenylanthracene (DPA)

In the foregoing examples, the number following the compound name indicates the emission wavelength.

In accordance with the present invention, the chromophore design (oxalate ester and fluorescer combination) has a high affinity for tumor tissue (e.g., breast tumor issue), a high fluorescence quantum yield, and transitions in a 800 nm to 1000 nm tissue transparency and scattering window. Chemical modifications to improve the selectivity to a specific type of tumor, for example a breast tumor, include chemical functionalization, linkage to monoclonal antibodies and the use of selective delivery vehicles (e.g., lipoproteins).

Figure 2:
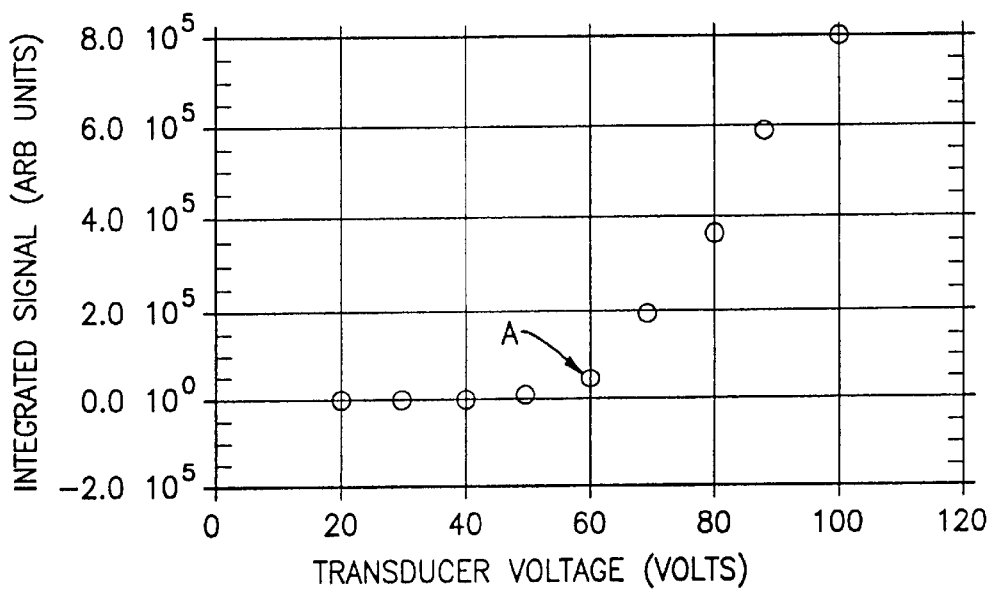
FIG. 2 is a graph that shows ultrasound-induced chemiluminescent intensity versus ultrasound transducer drive voltage, wherein the ultrasound energy is shown to be linear with voltage.

The inventor has experimentally determined that light is produced at appreciable levels, without the addition of hydrogen peroxide, when the ester bis (2,4-dinitrophenyl) oxalate (DNPO) and the fluorescer rubrene in the solvent dimethyl phthalate (DMP) are sonicated with an ultrasound bath 10, having an ultrasound transducer 12 operated at about 20 kHz. The ultrasound transducer 12 may generally be operated in the kilohertz to megahertz range. As is shown in FIG. 1, a greatest light intensity is observed at the antinodes 14 of the standing waves produced by the sonication bath. Additionally, and as shown in FIG. 2, a threshold behavior of the chemiluminescent intensity vs. ultrasound power (arrow "A" of FIG. 2 generally defines a threshold region) suggests that the reactive species initiating the reaction is produced via weak micro-scale cavitation.

Through a calorimetric assay it was determined that the irradiation of pure DMP solvent with ultrasound produced hydrogen peroxide at a rate of $8.4 \times 10^{-5}$ M/min. Therefore, applying ultrasound to DMP with DNPO produces the key intermediate via the action of $H_2O_2$ on the ester.

During chemiluminescent reactions the key intermediate is capable of transferring energy of several eV to the fluorescer. The inventor has realized that this transfer of energy can be used as a pathway to activate photosensitizers in PDT applications. The inventor has shown, in the above-identified U.S. Pat. No. 5,817,048 (U.S. patent application Ser. No. 08/821,088), that instead of transferring energy to a conventional fluorescer, the key intermediate is instead used to transfer energy to a selected PDT photosensitizer. In this manner the therapeutic action of the PDT compound can be realized without requiring light to be generated and delivered to the PDT compound. In this way the inventor has shown that a new modality for activating tumor-specific photosensitizers may be realized without the use of invasive lasers or other light sources. By employing these techniques within the present invention, in-vitro and in-vivo diagnostic and treatment applications can be achieved.

Figure 3:
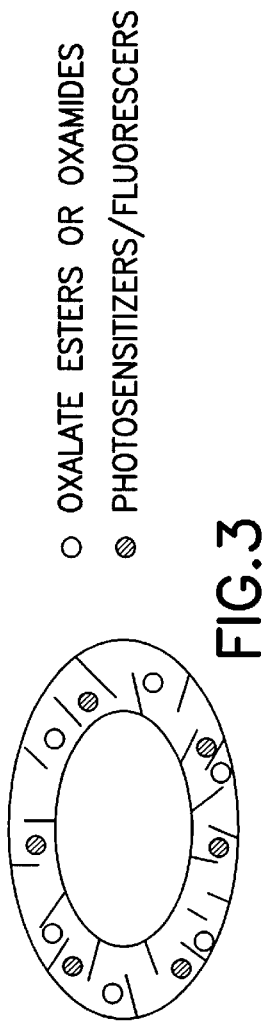
FIG. 3 is a schematic diagram of a biomimetic media employed in an in-vitro application of the present invention.

In accordance with the present invention, in-vitro applications include an aqueous environment in which sonochemical excitation of photosensitizers and fluorescent indicators occurs in a biomimetic media such as, for example, liposome/micelle suspensions (FIG. 3). As is shown in FIG. 3, the biomimetic media, i.e. a media that imitates a living organism or tissue, includes oxamides and fluorescers which when excited by the ultrasonic energy provide a fluorescent emission in a desired band of wavelengths. The desired band of wavelengths supports the transfer of energy to a photosensitive drug of interest.

During in-vivo diagnostic applications, a selected source of free radicals and a fluorescent photosensitizer compound can be delivered to a selected site by accumulation in rapidly dividing cells or by antigen binding. A combination of $O_2$ plus water or another hydrogen-containing solvent, for example DMP, plus acoustic energy yields free radicals (e.g., $H_2O_2$). The free radicals, in turn, react with an oxalate ester to generate a key intermediate. During a chemiluminescent reaction energy is transferred from the key intermediate to the fluorescent photosensitizer compound. The transferred energy activates the fluorescent photosensitizer compound to emit long wavelength light of a desired band of wavelengths.

In these diagnostic applications the emissions within the desired band of wavelengths are detected to indicate the presence of tissue abnormalities, for example, cancer cells or tumors. In one aspect of the present invention, the emissions are imaged to permit a visual inspection of a subject area of tissue for the tissue abnormalities which may represent cancer cells or tumors. Additionally, and as was noted previously, the above-identified U.S. patent and copending U.S. patent application disclose the use of the fluorescent emissions to activate the PDT compound to treat a targeted area of tissue.

It is also within the scope of the teachings of this invention to increase the oxygen concentration of the blood or tissues prior to and during the application of acoustic energy. By example, it is known to inject an emulsion into the blood stream to enhance ultrasound images made during an ultrasound scan. Such an emulsion is referred to as a contrast agent. One known emulsion for this purpose is based on the fluorocarbon dodecafluoropentane, and is referred to as EchoGen™ (Sonus Pharmaceuticals Inc.). After injection the emulsion changes from a liquid to a gas, and infuses the blood with microbubbles that are capable of traversing the lungs intact, and that are small enough to traverse capillaries that are 3 to 5 $\mu$m in diameter without damage. The microbubbles are exhaled through the lungs after a few moments. The microbubbles are about $10^5$ times more reflective than red blood cells to the ultrasound energy, and their presence serves to enhance the ultrasound image. The contrast agents may also be used to lower microcavitation power densities.

As noted above, the sono-chemical excitation of fluorescent photosensitizer compounds are employed within diagnostic applications to facilitate the diagnosis of cancer. In a diagnostic application, illustrated in FIG. 4, focused or scanned acoustic energy, in particular imaging ultrasound energy, is directed to a region of tissue to activate the fluorescent photosensitizer compounds disposed about a tumor located within the region. The activated fluorescent photosensitizer compounds trigger chemiluminescent reactions which emit long wavelength light (hv), as is discussed above.

That is, the focal point of the imaging ultrasound is directed about the region of tissue. As the focal point of the ultrasound is directed to a volume within the region where cancer cells or a cancer tumor is located, fluorescent photosensitizer compounds, disposed about the cancer cells, are activated to emit the fluorescent emission in the desired band of wavelengths. One or more optical detectors may be positioned about the region of tissue to detect the fluorescent emission and to indicate the present of the cancer cells or tumor.

It should be appreciated that as the ultrasound energy is focussed into the volume that coincides with the focal point of the imaging ultrasound, the threshold is reached, i.e. arrow "A" of FIG. 2, and the fluorescent photosensitizer compounds within the volume are activated to emit the detectable optical emission. In essence, the ultrasound source permits a focussed and localized volumetric effect enabling an accurate location of the tissue of interest.

It should also be appreciated that the source of the imaging ultrasound may, in fact, be two or more ultrasonic energy sources which may each output less than the critical energy intensity. Within a volume where the ultrasound energy from the two or more sources intersect, the critical intensity of ultrasonic energy may be reached to activate the fluorescent photosensitizer compounds.

Figure 4:
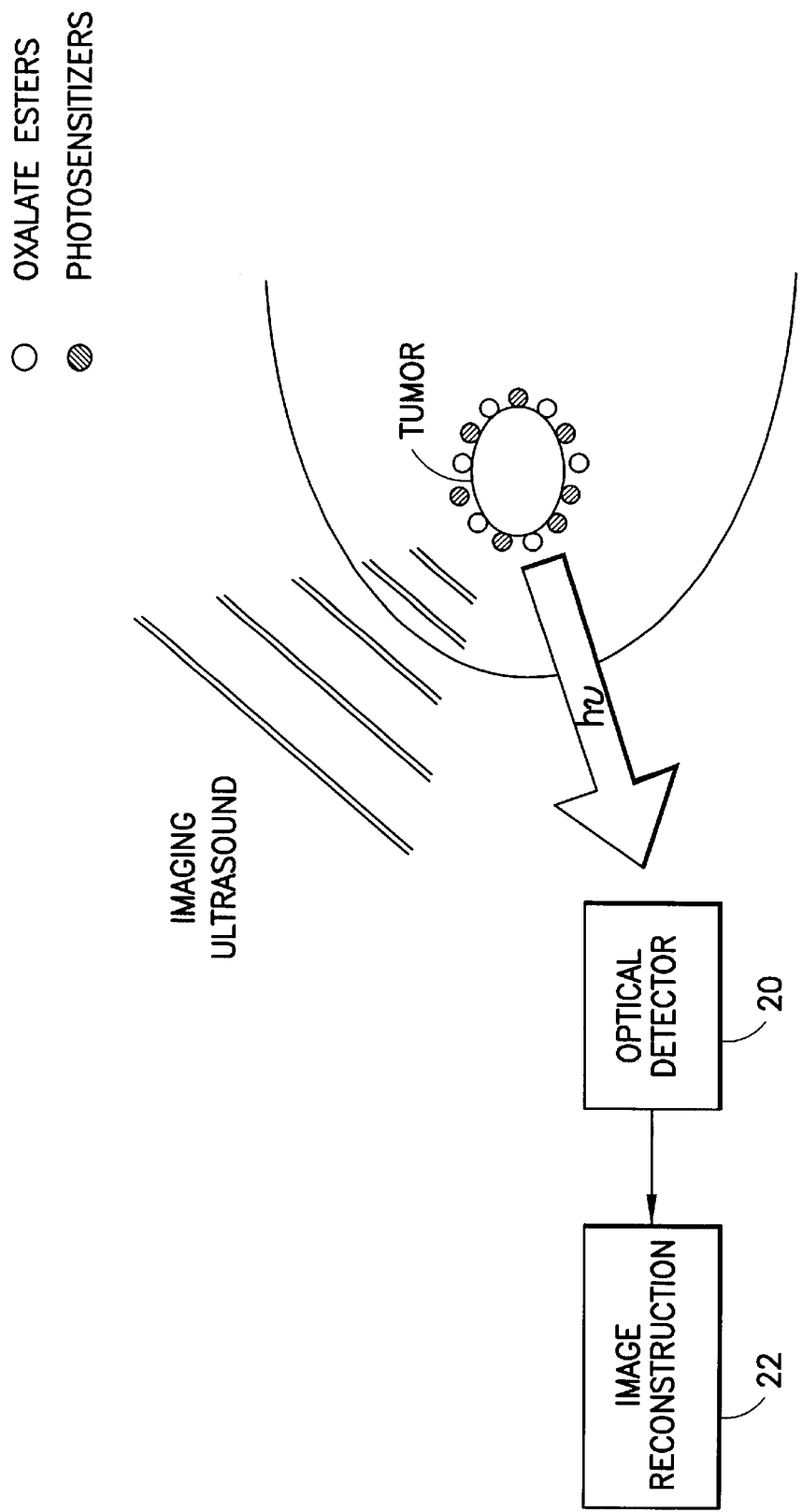
FIG. 4 is a schematic diagram of a diagnostic application of the present invention.

As shown in FIG. 4, an optical detector 20 (e.g., a sensitive photon counting system) maps the emissions (hv) from the chemiluminescent reactions to an image reconstruction unit 22. The image reconstruction unit 22 constructs an image of the region of interest, and in effect, an image of the tumor. In this non-evasive way, a tumor may be visually identified for treatment.

It should be appreciated that it is within the scope of the present invention to employ a broad beam of acoustic energy to activate fluorescent photosensitizer compounds within a region of tissue. A broad beam of, for example, imaging ultrasound energy permits the irradiation of a subject area of tissue emersed within an ultrasonic bath.

Figure 5A:
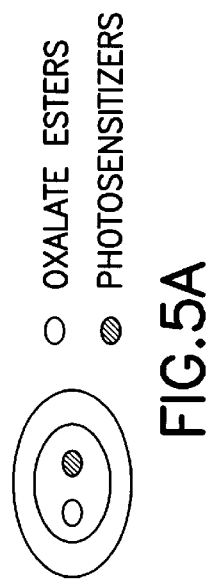
FIGS. 5A and 5B illustrate molecularly packaging techniques according to one aspect of the present invention.
Figure 5B:
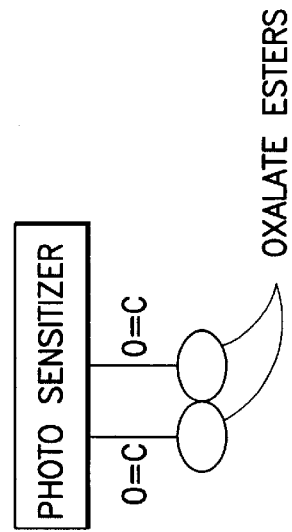

In one aspect of the present invention the transfer of energy to a fluorescent photosensitizer compound of interest is improved by employing a technique for molecularly packaging the oxalate esters and the photosensitizer. The molecular packaging promotes the efficient coupling of the molecules to maximize the transfer of energy. By maximizing the energy transfer, the amount of detectable light is increased. In one 0embodiment, shown in FIG. 5A, inclusion compounds such as, for example, cyclodextrins, micelles, and vesicles, include the oxalate esters and the photosensitizer. In another embodiment, shown in FIG. 5B, a molecular linkage is established between the oxalate esters and the photosensitizer.

While the invention has been particularly shown and described with respect to preferred embodiments thereof, it will be understood by those skilled in the art that changes in form and details may be made therein without departing from the scope and spirit of the invention.

What is claimed is:

1. A method for generating an image of a selected area of tissue, the method comprising the steps of:
   providing a fluorescent photosensitizer compound in combination with a hydrogen-containing solvent to the selected area of tissue;
   generating acoustic energy for generating free radicals from the solvent;
   reacting the free radicals with an oxalate ester to generate a key intermediate;
   transferring chemical energy to the fluorescent photosensitizer compound from the key intermediate;
   activating the fluorescent photosensitizer compound with the transferred energy to emit long wavelength light within a range of wavelengths; and
   detecting the long wavelength light to generate the image of the selected area of tissue; wherein the range of wavelenths minimize the absorption of the emissions by blood and melanin of the selected area of tissue and intervening areas of tissue.

2. A method as set forth in claim 1, wherein the solvent is comprised of dimethyl phthalate (DMP).

3. A method as set forth in claim 1, wherein the oxalate ester is comprised of ester bis(2,4-dinitrophenyl) oxalate (DNPO).

4. A method as set forth in claim 1, wherein the oxalate ester is comprised of bis(2,4,6-trichlorophenyl) oxalate.

5. A method as set forth in claim 1, wherein the acoustic energy is comprised of ultrasonic energy.

6. A method as set forth in claim 1, wherein the selected area of tissue is comprised of a selected area of living tissue, and the method comprises a further step of analyzing the image to identify a tumor within the living tissue.

7. A method as set forth in claim 6, wherein the step of activating further comprises an initial step of increasing an $O_2$ level of the living tissue.

8. A method as set forth in claim 1, wherein the method further comprising a step of molecularly packing the oxalate ester and the fluorescent photosensitizer compound to improve the transfer of energy.

9. A method as set forth in claim 8, wherein the step of molecularly packing is performed by forming an inclusion compound which contains the oxalate ester and the fluorescent photosensitizer compound.

10. A method as set forth in claim 9, wherein the inclusion compound is comprised of one of cyclodextrins, micelles and vesicles.

11. A method as set forth in claim 1, wherein the step of molecularly packing is performed by establishing a molecular linkage between the oxalate ester and the fluorescent photosensitizer compound.

12. A method for detecting a cell abnormality within a selected area of tissue, the method comprising steps of:

combining $O_2$, a hydrogen-containing solvent, and acoustic energy within the selected area of tissue to yield free radicals;

combining the free radicals, a fluorophore and an oxalate ester in a chemiluminescent reaction to generate emissions of long wavelength light having wavelengths in a range of wavelengths greater than about 390 nm; and detecting the long wavelength light to indicate a present of the cell abnormality;

wherein the oxalate ester and fluorescer combination has a high affinity for tumor tissue, a high fluorescence quantum yield and transitions in about a 800 nm to 1000 nm tissue transparency and scattering window.

13. A method as set forth in claim 12, wherein the free radicals are comprised of $H_2O_2$.

14. A method as set forth in claim 12, wherein the solvent is comprised of dimethyl phthalate (DMP).

15. An imaging system, comprising:

means for providing a fluorescent photosensitizer compound in combination with a hydrogen-containing solvent to a selected area of tissue;

means for generating acoustic energy and directing said acoustic energy to said selected area of tissue;

wherein said acoustic energy activates said fluorescent photosensitizer compound and said solvent to trigger chemiluminescent reactions which emit long wavelength light within a range of wavelengths;

a detector for detecting said long wavelength light; and an image reconstruction unit coupled to said detector for providing an image of said selected area of tissue; wherein said range of wavelenths minimize an absorption of said emissions by blood and melanin of said selected area of tissue.

16. A diagnostic method, comprising steps of:

applying a compound that is preselected to have an affinity for a tissue of interest;

applying acoustic energy to activate the compound; and detecting a presence of an optical emission from the activated compound, the optical emission having wavelengths in a range of wavelengths that is greater than ultraviolet radiation wavelengths and selected to minimize an absorption of said emissions by blood and melanin of said selected area of tissue.

* * * * *

UNITED STATES PATENT AND TRADEMARK OFFICE
CERTIFICATE OF CORRECTION

PATENT NO. : 6,233,481 B1
DATED : May 15, 2001
INVENTOR(S) : Nabil M. Lawandy

It is certified that error appears in the above-identified patent and that said Letters Patent is hereby corrected as shown below:

Claim 1,
Line 49, delete "wavelengths" and insert -- wavelengths --.

Claim 15,
Line 18, delete "wavelengths" and insert -- wavelengths --.

Signed and Sealed this

Twenty-eighth Day of August, 2001

Attest:

NICHOLAS P. GODICI
Attesting Officer
Acting Director of the United States Patent and Trademark Office